United States Patent
Bergmann et al.

(10) Patent No.: US 12,219,995 B2
(45) Date of Patent: Feb. 11, 2025

(54) VAPORIZER CARTRIDGE AND INHALER COMPRISING SUCH A VAPORIZER CARTRIDGE

(71) Applicant: KÖRBER TECHNOLOGIES GMBH, Hamburg (DE)

(72) Inventors: Max Bergmann, Hamburg (DE); Lasse Cornils, Hamburg (DE); Matthias Giese, Tokyo (JP); Christian Hanneken, Hamburg (DE); Jan Jaklin, Fellbach (DE); Marc Kessler, Hamburg (DE); Michael Kleine Wächter, Lankau (DE); Thomas Müller, Hamburg (DE); Niklas Romming, Hamburg (DE); Rene Schmidt, Buchholz i.d.N. (DE); Christof Schuster, Hamburg (DE); Tobias Wuttke, Reinbek (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 435 days.

(21) Appl. No.: 17/619,125

(22) PCT Filed: Jun. 17, 2020

(86) PCT No.: PCT/EP2020/066735
§ 371 (c)(1),
(2) Date: Dec. 14, 2021

(87) PCT Pub. No.: WO2020/254388
PCT Pub. Date: Dec. 24, 2020

(65) Prior Publication Data
US 2022/0354172 A1  Nov. 10, 2022

(30) Foreign Application Priority Data
Jun. 20, 2019 (DE) .......................... 102019116725.6

(51) Int. Cl.
*A24F 40/44* (2020.01)
*A24F 40/10* (2020.01)
(Continued)

(52) U.S. Cl.
CPC .............. *A24F 40/44* (2020.01); *A24F 40/10* (2020.01); *A24F 40/42* (2020.01); *A24F 40/46* (2020.01); *A61M 11/042* (2014.02)

(58) Field of Classification Search
CPC .......... A24F 40/10; A24F 40/42; A24F 40/44; A24F 40/46; A61M 11/042; A61M 15/06;
(Continued)

(56) References Cited

U.S. PATENT DOCUMENTS 10,272,170 B2 *  4/2019  Dubief .................. A24F 40/485
10,986,868 B2 *  4/2021  Chen ........................ H05B 3/34
(Continued)

FOREIGN PATENT DOCUMENTS

DE  102017123870 A1  4/2019
EP     3200559 A2     8/2017
(Continued)

OTHER PUBLICATIONS

International Search Report dated Sep. 22, 2020; International Application No. PCT/EP2020/066735.

*Primary Examiner* — Abdullah A Riyami
*Assistant Examiner* — Thang H Nguyen
(74) *Attorney, Agent, or Firm* — DINSMORE & SHOHL LLP (57) ABSTRACT

A vaporizer cartridge for an inhaler has a hollow body with a continuous flow channel and liquid storage tank. The tank has an access opening to the channel and a vaporizer unit extending over the entire access opening. The vaporizer unit has a wick member and a heating member. The vaporizer unit is liquid-permeable such that liquid is conveyed at least (Continued)

initially in a capillary manner from the storage tank through the vaporizer unit in the direction of the flow channel. The wick member is formed from a plurality of granular grains which, as a result of their fill and/or formation, form microchannels which establish a fluid connection between the storage tank and the flow channel, continuously from an entry side to an exit side of the wick member. An additional securing means is provided which is holds the granular wick member in position. A corresponding inhaler is also provided.

13 Claims, 5 Drawing Sheets (51) Int. Cl.
*A24F 40/42* (2020.01)
*A24F 40/46* (2020.01)
*A61M 11/04* (2006.01)

(58) Field of Classification Search
CPC .. A61M 2016/0015; A61M 2205/7545; A61M 2205/8206
See application file for complete search history.

(56) References Cited

U.S. PATENT DOCUMENTS

| | | | |
|---|---|---|---|
| 11,278,687 B2* | 3/2022 | Sudlow | A24F 40/44 |
| 11,357,262 B2* | 6/2022 | Rogan | A24F 40/42 |
| 11,547,817 B2* | 1/2023 | Schmidt | A24F 40/44 |
| 2014/0238424 A1* | 8/2014 | Macko | A24F 40/44 131/328 |
| 2016/0316819 A1* | 11/2016 | Zhou | C03C 11/00 |
| 2017/0215481 A1* | 8/2017 | Li | H05B 3/42 |
| 2017/0367411 A1* | 12/2017 | Duc | A24F 40/44 |
| 2019/0328039 A1* | 10/2019 | Romming | A61M 11/042 |
| 2021/0186097 A1* | 6/2021 | Schmidt | A61M 15/06 |

FOREIGN PATENT DOCUMENTS

| | | |
|---|---|---|
| EP | 3417726 A1 | 12/2018 |
| GB | 2561867 A | 10/2018 |
| WO | 2013083638 A1 | 6/2013 |
| WO | 2018211035 A1 | 11/2018 |

* cited by examiner

VAPORIZER CARTRIDGE AND INHALER COMPRISING SUCH A VAPORIZER CARTRIDGE

CROSS-REFERENCE TO RELATED APPLICATIONS

This application is the U.S. National Stage of PCT/EP2020/066735 filed Jun. 17, 2020, which claims priority to German Patent Application No. 102019116725.6, filed Jun. 20, 2019, the content of both are incorporated herein by reference in their entirety.

FIELD OF THE INVENTION

The invention relates to a vaporizer cartridge as a component of an inhaler, comprising a hollow body with a continuous flow channel as well as a storage tank for storing liquid, wherein the storage tank has at least one access opening to the flow channel and a vaporizer unit extending over the entire access opening is arranged in the region of each access opening, which vaporizer unit has a wick member and a heating member, wherein the vaporizer unit is formed to be liquid-permeable in such a manner that liquid can be conveyed at least initially in a capillary manner from the storage tank through the vaporizer unit in the direction of the flow channel.

The invention furthermore relates to an inhaler, configured and adapted for the inhalation of vapour enriched with active ingredients, comprising a cartridge carrier at least comprising an electronic control unit and an energy source as well as a vaporizer cartridge.

BACKGROUND OF THE INVENTION

Such vaporizer cartridges and inhalers are used in the luxury goods/stimulants industry, here in particular in the context of an electronic cigarette, what is known as an E-cigarette, and in the medical sector in order to be able to inhale liquid beverages and tobacco and/or liquid medical products in vapour form and/or as aerosols. During consumption, a person normally sucks on a mouthpiece of the inhaler, as a result of which a suction pressure arises in an air flow channel, which suction pressure generates an air flow through the air flow channel. The air flow can, however, also be generated by machine, for example, by a pump. In the flow channel, a liquid which is generated by the vaporizer unit and provided in a vaporized form is added as a gas phase to the air flow and subsequently recondensed in a targeted manner during mixing with the air flow in order to administer an aerosol or an aerosol-vapour mixture to the consuming person. The liquid is stored at or in the vaporizer cartridge. Various mixtures with various components of the same or different vapour densities are used as the liquid. A typical mixture for use in an E-cigarette has, for example, components of glycerine and propylene glycol, where applicable, enriched with nicotine and/or almost any desired flavouring agents. The mixture can correspondingly have medical components and active ingredients for use in the medical or therapeutic sector, i.e. for the inhalation of asthma preparations.

The individual components of the vaporizer cartridge, namely the hollow body, the storage tank and the vaporizer unit can be combined in a joint component, wherein this component is a single-use article which is designed for a finite number of inhalations by a consuming person and together with a cartridge carrier as a reusable multi-use article which at least comprises an electronic control unit and an energy source forms an inhaler. The vaporizer cartridge can, however, also only be formed by the joining together of several components, wherein individual components, namely in particular the hollow body and the vaporizer unit are arranged in the cartridge carrier as a multi-use article, and the storage tank as a separate component forms the single-use article. Finally, the inhaler can be used variably by replacing the single-use article which normally contains the liquid.

The single-use article and the multi-use article are correspondingly connected detachably to one another. The cartridge carrier as a multi-use article normally at least comprises an electronic control unit and an energy source. The energy source can be e.g. an electrochemical single-use battery or a rechargeable electrochemical battery, e.g. a Li-ion battery by means of which the heating member is supplied with energy via electrical contacts of the vaporizer unit. The electronic and/or electrical control unit serves to control the vaporizer unit within the vaporizer cartridge. The cartridge carrier can, however, also comprise components of the vaporizer cartridge. The single-use article can be formed so as to be capable of being plugged as a plug-on part onto the multi-use article or inserted as an insertion part into the multi-use article. Instead of a plug-type connection, screw connections or other quick connections can also be used. A mechanical and electrical coupling for the formation of a functionally ready inhaler is produced with the connection of single-use article and multi-use article.

The central component which ultimately determines the use (e.g. as an E-cigarette or as a medical inhaler) is the storage tank as a component of the vaporizer cartridge. This generally contains the liquid selected, desired and/or required by the person or a liquid mixture (also referred to generally below as fluid) as well as the hollow body that forms the flow channel and the vaporizer unit. The fluid is stored in the storage tank of the vaporizer cartridge. The fluid is conveyed by means of the liquid-permeable vaporizer unit out of the storage tank as a result of at least initially capillary conveyance through the wick member and the heating member. The voltage generated by the energy source which is applied to the heating member leads to a flow of current in the heating member. As a result of the heating resistance, preferably the ohmic resistance of the heating member, the flow of current leads to a heating of the heating member and ultimately to a vaporization of the fluid located in the vaporizer unit. The gas vapour generated in this manner or the vapour and/or aerosol escapes from the vaporizer unit in the direction of the flow channel and is recondensed to an aerosol in a targeted manner by mixing with the air flow. The fluid thus has a defined path with a defined direction of flow, namely as fluid through the wick member to the and through the heating member and as gas/vapour/mist and/or aerosol out of the heating member into the flow channel. In the flow channel, the vaporized fluid is carried along by the air flow if a pressure/vacuum acts on the flow channel, by virtue of the fact that e.g. a consuming person sucks on the flow channel or a pump conveys an air flow through the flow channel.

So that the fluid does not flow directly out of the storage tank into the flow channel, the vaporizer unit entirely covers the access from the storage tank to the flow channel. Entirely covers means in this context that the liquid is necessarily guided through the vaporizer unit so that the fluid cannot travel directly from the storage tank into the flow channel, but rather must take the "detour" via the wick member and the heating member. The wick member serves on the one hand the purpose of intermediate storage of fluid in order to still make available sufficient fluid for a few draws on the inhaler in particular in the case of an almost empty storage tank. The wick member serves on the other hand in particular the purpose of transporting the fluid from the storage tank in the direction of the flow channel and acts simultaneously as a type of non-return protection in order to prevent the return flow of fluid and/or vapour in the direction of the storage tank.

Hitherto known vaporizer cartridges have a vaporizer unit with a wick member which is formed from several threads/fibres which are interwoven/twisted with one another composed e.g. of cotton wool or glass fibres. This fibre wick has capillary properties which lead, upon initial contact with the fluid, to the fibre wick dipping into the storage tank, and the fluid in the storage tank being absorbed and conveyed in the direction of the heating member. The heating member is normally formed in the form of a spiral-wound filament. This wound metal wire is composed, for example, of stainless steel, copper, copper compounds or nickel. This vaporizer unit can generally only be produced manually and has a limited storage capacity for intermediate storage of fluid. A further disadvantage lies in the low transport rate of fluid as a result of the limited number of microchannels and a non-homogeneous temperature distribution which arises due to the system over the length of the wick-spiral coil system. In other words, a uniform and continuous supply of the heating member with the fluid is only ensured to a limited extent. Moreover, this solution does not have non-return protection.

In the case of other known solutions, the vaporizer unit therefore comprises a one-piece wick block as the wick member. This wick block normally composed of ceramic materials simplifies the automated production of the vaporizer unit and the vaporizer cartridge and has several microchannels for a transport rate which is increased in comparison with the fibre wick. Nevertheless, this solution also has several disadvantages. In addition to a still limited transport rate and intermediate storage capacity, the use of such block-like wick blocks is very inflexible and above all difficult to mount since the wick blocks can only be used in exactly prefabricated—in a narrow tolerance range—receivers/holders or the like.

In the case of a one-piece wick body, this itself can serve as a heating member if the e.g. ceramic material of the wick body which has microchannels is formed to be electrically conductive. The wick body then has a dual function and forms the vaporizer unit. In other cases, in addition to the wick body, a separate component can serve as a heating member. In the latter case, the wick body and the separate heating member form the vaporizer unit. The heating member can have at least one semi-conductor material and/or a doped semi-conductor material, preferably a p- or n-doped semi-conductor material, for example, mono- or polycrystalline silicon and/or mono- or polycrystalline p- or n-doped silicon. The heating member can, however, also be composed of silicon. The heating member is then normally a laminar or flat MEMS component (Micro-electro-mechanical-system component) which is formed to be liquid-permeable. In both cases, the wick body is clamped in particular by clamping on the hollow body or between the hollow body and other components of the vaporizer cartridge. In particular, a reproducible securing of the wick body by means of interference fit is difficult due to manufacturing tolerances.

SUMMARY OF THE INVENTION

According to the invention, in order to overcome the above-mentioned disadvantages, instead of the fibre wick or the one-piece wick block, a wick member should be used as the wick body, which wick member is formed from a plurality of granular grains. Such a granular wick member cannot be readily held, in particular clamped in position with conventional means.

The object on which the invention is based is to propose a vaporizer cartridge which overcomes the stated disadvantages with a granular wick member which is held in its position in a simple and secure manner. The object furthermore lies in proposing a corresponding inhaler.

This object is achieved by a vaporizer cartridge of the above-mentioned type in that the wick member is formed from a plurality of granular grains which, as a result of their fill and/or formation, form microchannels which extend, in order to establish a fluid connection between the storage tank and the flow channel, continuously from an entry side $E_D$ of the wick member to an exit side $A_D$ of the wick member, wherein an additional securing means is provided which is configured and adapted to hold the granular wick member in position in the region of the access opening in a manner which maintains the fluid connection. The term fill describes the grains lying next to one another both loosely and in a connected manner, wherein shaken and/or compressed arrangements of the grains are also covered by this term. The term formation of the grains describes, for example, that the grains themselves can have micro-cavities and/or microchannels. The microchannels are formed by the grains which lie against one another. A plurality of random microchannels between the storage tank and the flow channel which ensure a constant and uniform vaporization on the exit side of the vaporizer unit are thus formed in the vaporizer unit between the individual grains and/or by individual grains. In other words, an optimum fluid coupling between the entry side into the vaporizer unit and the exit side out of the vaporizer unit is established by the granular wick member. The additional "securing means" describes initially in a general manner anything which can hold the grains as a wick member in position, therefore, among other things, mechanical, physical, chemical, magnetic or electrostatic securing options or combinations thereof.

A wide range of advantages are achieved in comparison with the solutions known from the prior art with the configuration according to the invention of the granular wick member. In addition to the improved transport rate, more fluid and above all fluid is conducted in a uniform manner from the storage tank through the vaporizer unit, the granular wick member ensures an increased intermediate storage capacity for fluid as a result of the granular and thus porous wick structure. A granular wick member furthermore improves the non-return protection since the formed microchannels have a non-linear profile. The mounting of a granular wick member is particularly advantageous since this can be adapted at the respective mounting location to any desired contour/geometry of the receiver of the wick member. As a result of the grain structure, the wick member adapts during mounting/filling of the granular material flexibly to the respective contour/geometry and fills the cavities formed by the respective contour/geometry—not forming microchannels—and avoids the formation of gaps to adjoining surfaces. As a result, constant and reproducible vaporization conditions are ensured by the granular wick member. It does not play any role here whether the vaporizer unit—with the wick member and/or the heating member as a component of the vaporizer cartridge—is arranged on or in the cartridge carrier, i.e. on/in the mutli-use article, or whether the vaporizer unit is arranged on/in the single-use article. The additional securing means enables on the one hand an automated mounting/production of the vaporizer cartridge, therefore in particular the automatic positioning of the wick member in the region of the access opening, and on the other hand the holding of the position of the granular wick member in the region of the access opening.

One preferred embodiment is characterised in that the securing means is of a mechanical type such that a receiving chamber enclosed on all sides with an opening for the introduction of the granular wick member is formed from components of the vaporizer cartridge or parts thereof and the opening is closed with a cover element, wherein the receiving chamber is formed to be liquid-permeable at least in sections. The granular grains fill the receiving chamber to a maximum extent, preferably without undesirable cavities and/or gaps—not forming microchannels—so that the wick member can be adapted to almost any form of the surroundings independently on the manufacturing tolerances. The liquid-permeable sections of the receiving chamber are formed in particular in the direction of the storage tank and in the direction of the flow channel. The opening in the receiving chamber enables the automated introduction/filling of the wick member into the receiving chamber. The granular wick member is held in its final position with the cover element. The cover element itself can also be formed to be liquid-permeable.

The vaporizer cartridge advantageously comprises a carrier element which forms the hollow body and on the one hand has a through-opening for forming the flow channel and on the other hand has a recess for receiving the wick member, wherein the recess forms the side walls of the receiving chamber and the recess towards the storage tank and towards the flow channel is delimited in each case by a liquid-permeable structure. The structure, e.g. a grid structure, towards the storage tank is preferably the cover element. Any structure can be formed from metal, plastic, fleece or other flexible and inflexible materials or material mixtures. The carrier element itself thus forms a part of the securing means which is completed by (grid) structures, heating members or other liquid-permeable components. The actual retaining element of the wick member which holds it in the recess is the cover element which is connected to the carrier element. The receiving chamber as a component of the securing means holds together the wick member and the heating member in the event that a separate heating member to the wick member is provided and in position, and indeed in front of the access opening between storage tank and flow channel, so that the liquid on the one hand is reliably prevented from flowing directly out of the storage tank into the flow channel, and on the other hand is conducted in a uniform manner and constantly in the direction of the flow channel.

One expedient further development is characterised in that the grains of the granular wick member are held in position by a sieve in such a manner that the sieve, together with the side walls delimiting the receiving chamber and a heating member formed separately from the wick member, encloses the volume of the wick member. This embodiment enables the simple and automated introduction of the wick member into the receiving chamber and the holding in position of the wick member in the receiving chamber. In particular, the sieve as a retaining element can engage on the one hand into at least one part of the grains and on the other hand maintain the fluid connection between the storage tank and the wick member.

The cover element is preferably optionally a solid or soft lid. For example, a sieve formed from metal can be used as a solid lid. A soft lidcan be e.g. a liquid-permeable silicon stopper or a simple fleece strip.

In one preferred further development, the lid covers at least the opening, preferably, however, the lid covers the entire hollow body including the opening of the receiving chamber, wherein the lid is formed to be liquid-permeable at least in sections. Simple and secure positioning and holding of the wick member in position are ensured with this lid.

In a further preferred embodiment, the lid is a sleeve which is displaceable in a longitudinally axial or rotational manner with respect to the hollow body and which is formed to be liquid-permeable at least in sections. Simple and secure positioning and holding of the wick member in position are ensured with the sleeve.

In a further preferred further development, the lid has a wound fleece strip or the lid is formed from a wound fleece strip. The fleece strip as a retaining element is particularly lightweight and holds the wick member in position, alongside optimum liquid permeability.

In a further preferred embodiment, the securing means is of a physical and/or chemical type such that the grains can be held in position by melting and/or precipitation-hardening processes. This type of securing means can be combined with mechanical securing means or parts thereof. By fusing the grains with one another and/or with adjacent structures, for example, the carrier element, a secure retention means for the wick member can be formed.

Grains of the granular wick member are advantageously fused directly with the hollow body or the carrier element. Simple and secure fixing of the granular wick member is thus ensured.

One expedient further development provides that fused grains of the granular wick member form their own closed receiving chamber which is liquid-permeable at least in sections. Simple and secure fixing of the granular wick member is thus likewise ensured.

At least the cover element is preferably formed from fused grains from at least one part of the granular wick member. With this configuration, the wick member itself or parts thereof form its retaining means to hold the wick member in position.

In a further preferred embodiment, the securing means is of a magnetic type such that the grains are formed to be at least partially magnetic and magnets which are arranged in the region of the wick member hold the grains in position.

In a further preferred embodiment, the securing means is of an electrostatic type such that the grains are at least partially electrically charged and electric fields which are present in the region of the wick member hold the grains in position.

The securing means are preferably configured and adapted optionally for a permanent or a temporary securing. One example of a permanent securing means is a lid which can be plugged on, which in the plugged-on state prevents loose grains filled into the receiving chamber from falling out of the receiving chamber. In other words, the lid holds the grains in position. One example of a temporary securing means is the wick member as a block at least for mounting purposes of the vaporizer cartridge formed from a frozen or shock-frozen liquid/granulate paste. This frozen or shock-frozen block holds the grains together for the period of mounting. This block can be introduced in an automated manner into the receiving chamber. The receiving chamber can be closed with a lid so that the loose grains of the wick member are held in position after thawing out.

The object is also achieved by an inhaler of the above-mentioned type in that the vaporizer cartridge is configured and adapted described herein.

The advantages which arise from this have already been described in conjunction with the vaporizer cartridge, hence reference is made to the above statements to avoid repetition.

DESCRIPTION OF THE DRAWINGS

Further expedient and/or advantageous features and further developments of the vaporizer cartridge and the inhaler will become apparent from the subordinate claims and the description. Particularly preferred embodiments of the vaporizer cartridge and the inhaler will be explained in greater detail on the basis of the enclosed drawing. In the drawing:

DETAILED DESCRIPTION OF THE PREFERRED EMBODIMENTS

The vaporizer cartridge represented in the drawing as well as the inhaler serve the purpose of inhalation of vapour enriched with active ingredients, e.g. nicotine, and/or aerosols from liquids and are correspondingly described in conjunction with an E-cigarette. The vaporizer cartridge and the inhaler can be used in the same manner to inhale vapour enriched with medical active ingredients from pharmaceutical products and/or food supplements.

The represented vaporizer cartridge 10 comprises a hollow body 15 with a continuous flow channel 16 as well as a storage tank 17 for storing liquid, wherein the storage tank 17 has at least one access opening 18 to the flow channel 16 and a vaporizer unit 19 extending over the entire access opening 18 is arranged in the region of each access opening 18, which vaporizer unit 19 has a wick member 20 and a heating member 21, wherein the vaporizer unit 19 is formed to be liquid-permeable in such a manner that liquid can be conveyed at least initially in a capillary manner from the storage tank 17 through the vaporizer unit 19 in the direction of the flow channel 16.

The hollow body 15 with its at least one flow channel 16 forms a suction channel/vent. The form of the hollow body 15 just like the profile of each flow channel 16 can be almost as desired. It is vital that entry side $E_S$ of each flow channel 16 is open to the surroundings, in order e.g. to be able to take in air, and that exit side $A_S$ is open in order to be able e.g. to apply a vacuum, in particular by the suction of a consuming person. Open means in this context that entry side $E_S$ and exit side $A_S$ are air-permeable. Two or more flow channels 16 with corresponding entry sides $E_S$ and exit sides $A_S$ can also be provided. In the region of the access opening 18 between the storage tank 17 and the flow channel 16, the vaporizer unit 19 forms a type of liquid stop means which prevents liquid flowing directly out of the storage tank 17 and as liquid into the flow channel 16. Irrespective of the form and formation of the storage tank 17, two or more storage tanks 17 can also be provided, and of the hollow body 15 and the arrangement/positioning of the storage tank 17 to the hollow body 15, the vaporizer unit 19 ensures that liquid is necessarily conducted out of the storage tank 17 in the direction of the flow channel 16 and at the latest when exiting from the vaporizer unit 19 is output as vapour into the or each flow channel 16.

This vaporizer cartridge 10 is characterised according to the invention in that the wick member 20 is formed from a plurality of granular grains 24 which, as a result of their fill and/or formation, form microchannels 23 which extend, for the establishment of a fluid connection between the storage tank 17 and the flow channel 16, continuously from an entry side $E_D$ of the wick member 20 to an exit side $A_D$ of the wick member 20, wherein an additional securing means 25 is provided which is configured and adapted to hold the granular wick member 20 in position in the region of the access opening 18 in a manner which maintains the fluid connection.

The grains 24 form on the one hand (micro-)cavities with adjacent grains 24. On the other hand, the grains 24 themselves can have (micro-)cavities, what are known as pores. As a result of the linking and the interaction of all the micro-cavities in the and/or between the grains 24, the microchannels 23 are formed which ensure an at least initially capillary conveyance and are formed continuously and have a non-linear profile. When passing through the vaporizer unit 19 comprising the wick member 20 and the heating member 21, during operation of the vaporizer cartridge 10, vapour and/or aerosol are formed from the liquid of the storage tank 17 towards the flow channel 16, wherein the porous structure of the wick member 20 on one hand forms a storage medium for liquid and on the other hand represents a flow resistance. The direction of flow of the liquid occurs from the storage tank 17 through the vaporizer unit 19 in the direction of the flow channel 16.

Additional "securing means" 25 describes initially in a general manner anything which can hold the grains 24, at least for the purpose of mounting, i.e. during the introduction of the wick member 20 into the region of the access opening 18, preferably, however, also in the mounted state of the vaporizer cartridge 10, as the wick member 20 in position, therefore, among other things, mechanical, physical, chemical, magnetic or electrostatic securing options or combinations thereof.

The vaporizer cartridge 10 according to the invention can as a single-use article be a structural unit which contains the components hollow body 15, storage tank 17 and vaporizer unit 19. The vaporizer cartridge 10 can, however, also be formed in multiple parts, wherein components of the vaporizer cartridge 10 are distributed to the single-use article and the multi-use article in such a manner that e.g. the storage tank 17 is a single-use article, which only leads to the structural unit of the vaporizer cartridge 10 upon combination with a cartridge carrier 13 that can be a multi-use article and can also comprise, in addition to an electronic control unit 11 and an energy source 12, components of the vaporizer cartridge 10, such as e.g. the hollow body 15 and the vaporizer unit 19. The vaporizer cartridge 10 is correspondingly defined via its components, namely hollow body 15 with flow channel 16, storage tank 17 and vaporizer unit 19, and not via the constructive/structural assignment of the components to the multi-use article or single-use article.

The features and further developments described below represent preferred embodiments as seen on their own or in combination with one another. It is expressly pointed out that features which are summarised in the claims and/or the description and/or the drawing or are described in a joint embodiment can also functionally independently further develop the vaporizer cartridge 10 described further above.

The vaporizer cartridge 10 is preferably configured and adapted for mechanical and electrical connection to the cartridge carrier 13 comprising at least the electronic control unit 11 and the energy source 12 for the formation of an inhaler 14, wherein the vaporizer unit 19 comprises electrical contacts 22 for electrical contact with the energy source 12. The inhaler 14 can be activated e.g. by an inhaling person, for example, as an E-cigarette, or e.g. by a pump, e.g. as a medical instrument in the event that the person himself or herself can no longer suck or not to an adequate extent.

In one preferred embodiment, the securing means 25 is of a mechanical type such that a receiving chamber 26 enclosed on all sides with an opening 27 for the introduction of the granular wick member 20 is formed from components of the vaporizer cartridge 10 or parts thereof and the opening 27 is closed with a cover element 28, wherein the receiving chamber 26 is formed to be liquid-permeable at least in sections. With the receiving chamber 26, a volume or a type of cage is formed into which the wick member 20 can be introduced and can be held in position by the cover element 28. The wick member 20 can be filled as a loose fill of the grains 24 into the open receiving chamber 26 or used as composite grains in the open receiving chamber 26, wherein the wick member 20 in the mounted state of the vaporizer cartridge 10 is held in position by the cover element 28, and indeed in the access opening 18 between the storage tank 17 and the flow channel 16. The securing means 25 of a mechanical type fully encloses the wick member 20 and simultaneously ensures a fluid connection to the storage tank 17 on the one hand and in the direction of the flow channel 16 on the other hand. The mechanical securing means 25 is a retaining element which can be in engagement with at least a part of the grains of the wick member 20.

The vaporizer cartridge 10 preferably comprises a carrier element 29 which forms the hollow body 15 and on the one hand has a through-opening 30 for forming the flow channel 16 and on the other hand has a recess 31 for receiving the vaporizer unit 19, wherein the recess 31 forms side walls 32 of the receiving chamber 26 and the recess 31 towards the storage tank 17 and towards the flow channel 16 is delimited in each case by a liquid-permeable structure. The vaporizer unit 19 can be formed solely by the wick member 20 which simultaneously represents the heating member 21 in the event that the grains 24 are formed to be at least partially electrically conductive. In order to hold the wick member 20 in position, i.e. in the recess 31, e.g. a structure, e.g. a grid structure, is then necessary. The vaporizer unit 19 is, however, preferably formed in two pieces in such a manner that the wick member 20 and the heating member 21 are separate elements. In the latter case, e.g. the heating member 21 forms the liquid-permeable structure towards the flow channel 16.

Figure 2:
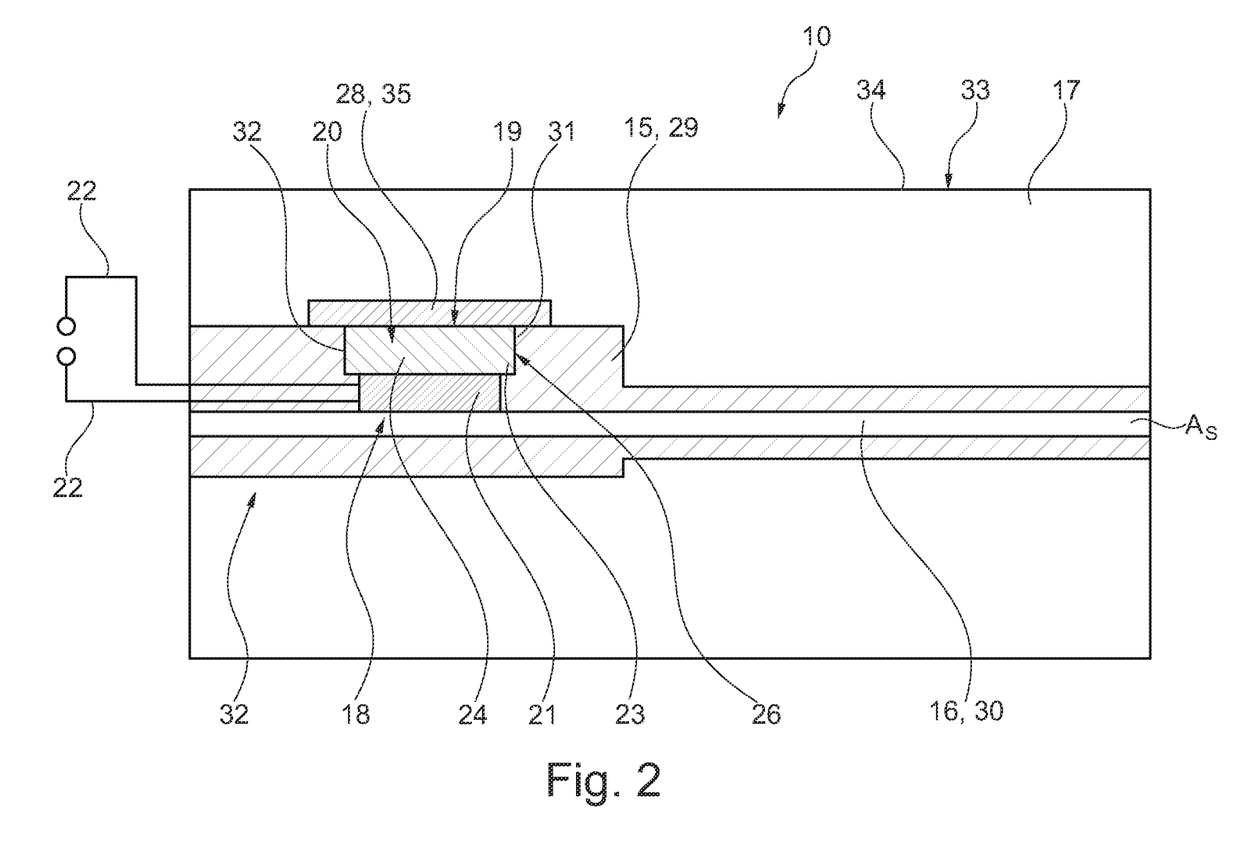
FIG. 2 shows an enlarged representation of the vaporizer cartridge according to FIG. 1 in partial section.

The carrier element 29 is preferably a tubular body. The carrier element 29 can, however, also have different forms. The recess 31 in which the vaporizer unit 19 is arranged is formed in the circumferential wall of the body. The unit 32 formed from carrier element 29 and vaporizer unit 19 is preferably arranged within a housing 33 which forms the storage tank 17, wherein the inner volume of the storage tank 17 is formed between a housing wall 34 of the housing 33 and the carrier element 29. The carrier element 29 can extend only partially through the housing 33. In other embodiments, the carrier element 29 can also extend completely (see e.g. FIG. 2) through the housing 33.

In another embodiment, the grains 24 of the granular wick member 20 are held in position by a sieve in such a manner that the sieve, together with the side walls 32 delimiting the receiving chamber 26 and a heating member 21 formed separately from the wick member 20, encloses the volume of the wick member 20. In simple terms, the receiving chamber 26 is delimited to the sides and at the bottom by the side walls 32 and the heating member 21 in order to bring, fill or otherwise insert the wick member 20—preferably in an automated manner—from above into the receiving chamber 26 through the opening 27. The receiving chamber 26 filled out by the wick member 20 is closed by means of the sieve. The heating member 21 through liquid-permeable passages and the sieve through its grid-like and/or porous structure represent the fluid connection between the storage tank 17 and the flow channel 16.

The cover element 28 serves quasi as a lid 35, wherein the lid 35 is optionally a solid or soft lid 35. The lid 35 is attached detachably or non-detachably above the opening 27 such that the granular material, i.e. loose grains 24 or grains 24 connected to one another, is held reliably in position. The lid 35 covers at least the opening 27. In other embodiments, the lid 35 surrounds, however, the entire hollow body 15 or the carrier element 29 including the opening 27 of the receiving chamber 26, wherein the lid 35 is liquid-permeable at least in sections, i.e. is formed by a perforation. The lid 35 is not restricted to a classic lid form, but rather can have any desired forms. As mentioned, the lid 35 can also be composed of different materials and material combinations.

Figure 6:
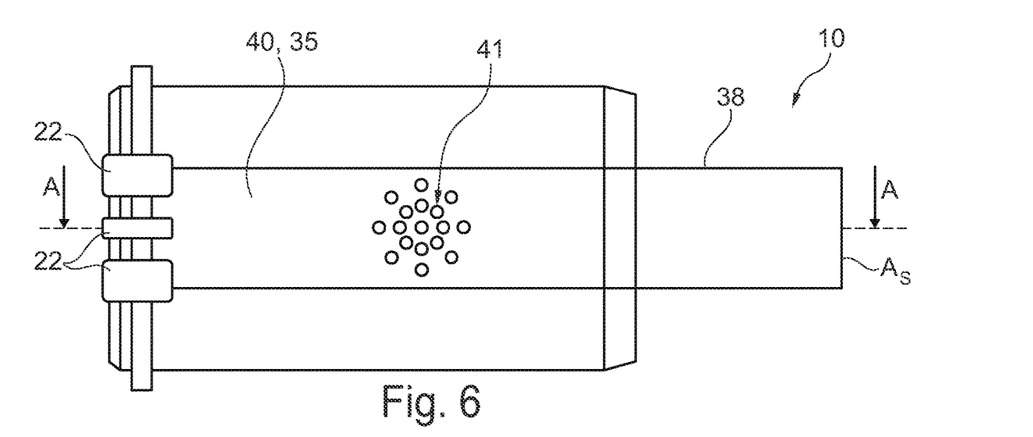
FIG. 6 shows an enlarged representation of a further embodiment of a part of a vaporizer cartridge.
Figure 7:
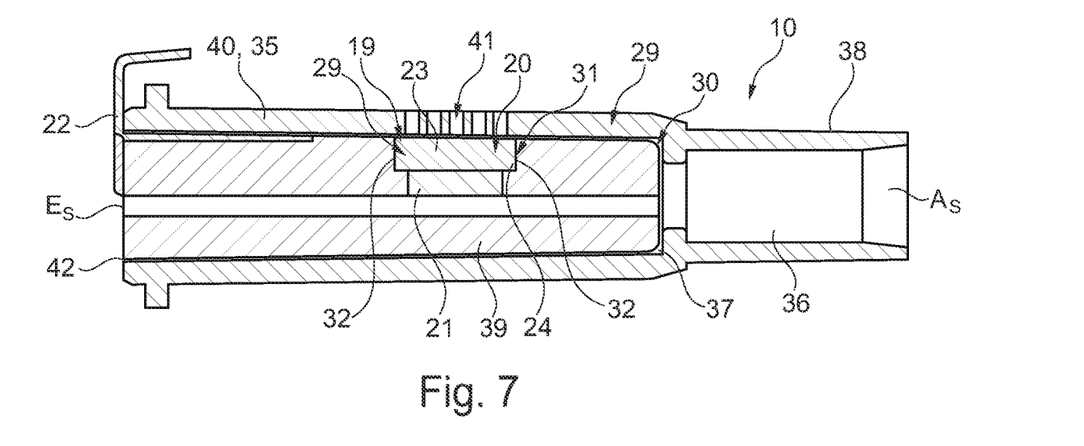
FIG. 7 shows the vaporizer cartridge according to FIG. 6 along section A-A.

A solid lid 35 composed e.g. of plastic can be inferred from FIGS. 6 and 7. In this embodiment, the carrier element 29 is formed to be tubular with the through-opening 30. Two chambers 36, 37 connected to one another are formed within the through-opening 30. One chamber 36 serves as mouthpiece 38. An insert 39 which bears the vaporizer unit 19 with the heating member 21 and the wick member 20 is arranged in the second chamber 37. The insert 39 has the recess 31 by which the side walls 32 are formed in order to define the receiving chamber 26. The vaporizer unit 19 and thus also the wick member 20 are held in position by the insert 39 and the inside of a wall 40 of the carrier element 29. The wall 40 of the carrier element 29 thus forms the hard lid 35. The insert 39 furthermore has a through-opening 42 which is operatively connected to the first chamber 36 in order to form the flow channel 16. The carrier element 29 has, in the wall 40 in the region against which the wick member 20 abuts on the inside of the wall 40 of the tubular carrier element 29, a perforation 41 which ensures a liquid coupling to the storage tank 17. The storage tank 17 is correspondingly formed between the housing wall 34 of the housing 33 and the wall 40 of the carrier element 29.

The lids 35 can be formed in various ways. In addition to the described variants, it is, for example, possible to form the lids 35 from a precipitation-hardened material ply, e.g. a precipitation-hardened grid, or from a (polyetheretherketone) PEEK sieve which is welded to the carrier element 29 in order to close the opening 27 of the receiving chamber 26.

Figure 3:
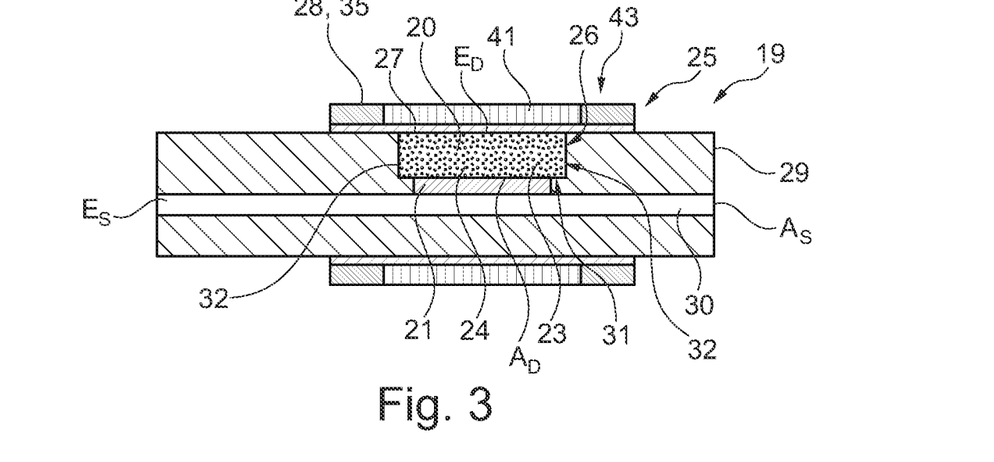
FIG. 3 shows an enlarged representation of a preferred embodiment of a part of a vaporizer cartridge in section.
Figure 4:
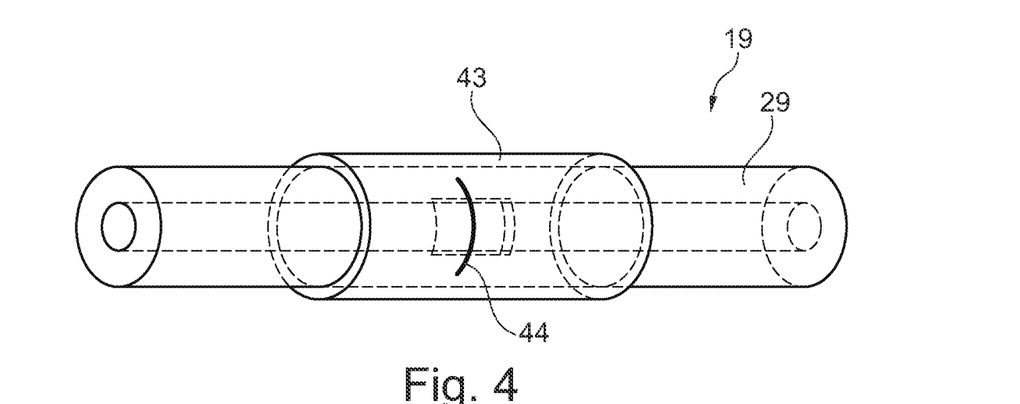
FIG. 4 shows a further embodiment of a part of a vaporizer cartridge.
Figure 5:
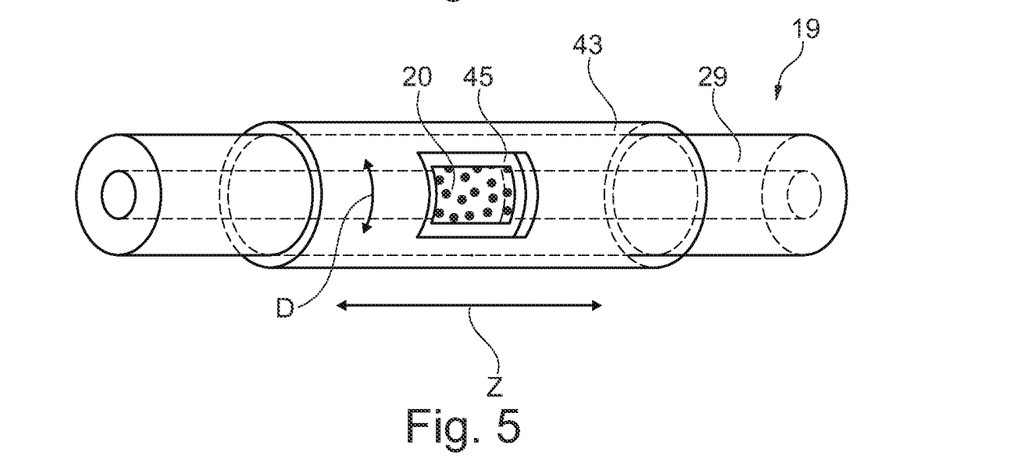
FIG. 5 shows a further embodiment of a part of a vaporizer cartridge.

A soft lid 35 is represented by way of example in FIGS. 3 to 5. The lid 35 is a sleeve 43 which is displaceable in a longitudinally axial or rotational manner with respect to the hollow body 15 which is preferably formed to be cylindrical as the carrier element 29 and which is formed to be liquid-permeable at least in sections. In other words, the sleeve 43 for covering the wick member 20 and holding it in position can be rotated about the longitudinal axis or displaced along it. The hollow body 15 can, however, also have other forms and be formed e.g. to be oval. The sleeve 43, which can also be composed of a hard material, is preferably formed to be flexible and can form a plastic or silicon ring with liquid-permeable portions which can form a perforation 41. For example, FIG. 3 represents a tubular carrier element 29 with a continuous through-opening 30 which, in the recess 31, bears the two-part vaporizer unit 19. Precisely one elastic sleeve 43 can be adapted to various forms/contours of the hollow body 15.

The vaporizer unit 19 is held in the recess 31 by the elastic sleeve 43 which is formed to be liquid-permeable at least in the region of the wick member 20. FIGS. 4 and 5 represent in each case a tubular carrier element 29, in the case of which the vaporizer unit 19 is likewise held in position by an elastic sleeve 43. In FIG. 4, the sleeve 43 covers the wick member 20. The sleeve 43 has, however, a slit 44 which opens by pulling (see arrow Z) on the sleeve 43 to a window 45 (see FIG. 5) in order to release the wick member 20. Instead of the slit 44, in principle, the window 45 can be provided which can be moved by rotation (see arrow D) or pushing of the sleeve 43 out of a position in which the sleeve 43 covers the wick member 20 into a position in which the window 45 lies above the wick member 20. The sleeve 43, which can also be a tube, is preferably formed from silicon. In other embodiments, the lid 35 has a wound fleece strip or is formed from a wound fleece strip. The lid 35 can furthermore also be a plaster, a grid, a shrink hose or the like.

The lid 35, i.e. the element, which holds granular wick member 20, formed e.g. from sand and/or graphite, in position can also be formed from an annular foam disc with a through-bore. Such a "foam donut" can be put in place from above with the through-bore via a tubular carrier element 29 such that the opening 27 of the receiving chamber 26 surrounding the vaporizer unit 19 and thus the wick member 20 is covered in the carrier element 29 by the foam ring so that the wick member 20 is held in its position. An open-pored nature of the foam ring provides the fluid connection to the storage tank 17.

Figure 8:
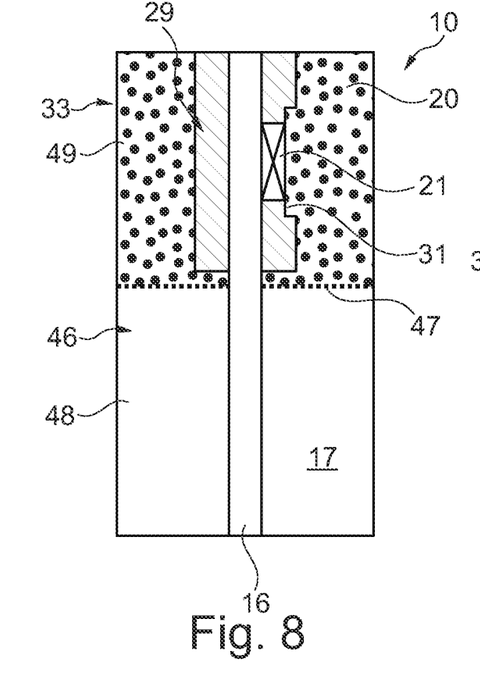
FIG. 8 shows an enlarged representation of a further embodiment of a vaporizer cartridge in partial section.
Figure 9:
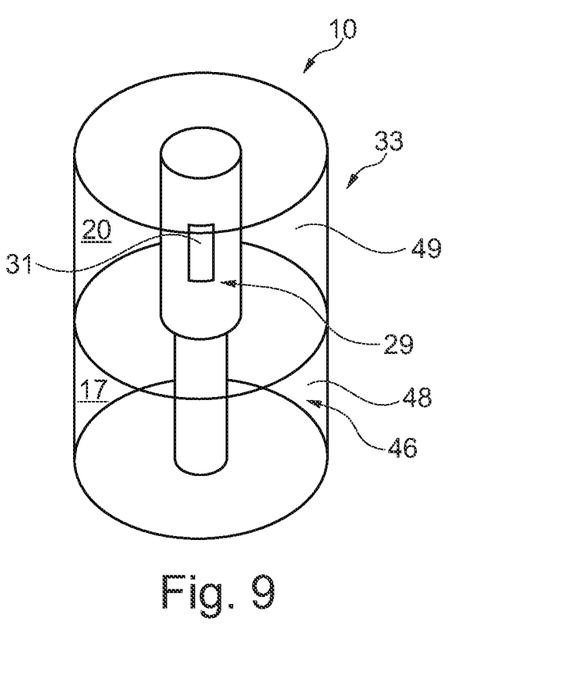
FIG. 9 shows the vaporizer cartridge according to FIG. 8.

FIGS. 8 to 11 show further embodiments of possible vaporizer cartridges 10. In the case of these embodiments, a cylindrical housing 33 which can also have any other form is provided to form an inner space 46 in which a continuous vent is provided as flow channel 16. The carrier element 29 extends over a part of the flow channel 16. The recess 31 in which the heating member 21 is arranged is formed in the carrier element 29. In the variant of FIGS. 8 and 9, a structure 47, preferably a grid structure, divides the inner space 46 into two regions 48, 49, wherein one region 48 serves as storage tank 17 for the liquid and a region 49 serves to receive the granular wick member 20 which is only indicated in FIGS. 8 and 10 for the sake of improved clarity and is not explicitly represented in FIGS. 9 and 11. In other words, the region 49 is entirely filled out with the granular grains 24 of the wick member 20, e.g. with sand. The region 49 can, however, e.g. also be filled out with the foam ring described above. The structure 47 is arranged below the carrier element 29 in such a manner that the wick member 20 entirely surrounds the carrier element 29 and correspondingly also covers the heating member 21. The securing means 25 of a mechanical type is correspondingly formed by the housing wall 34 of the housing 33, the carrier element 29, the heating member 21 as well as the structure 47 which jointly hold the wick member 20, here e.g. grains of sand, in position in front of the heating member 21. The structure 47 ensures the fluid connection to the storage tank 17.

Figure 10:
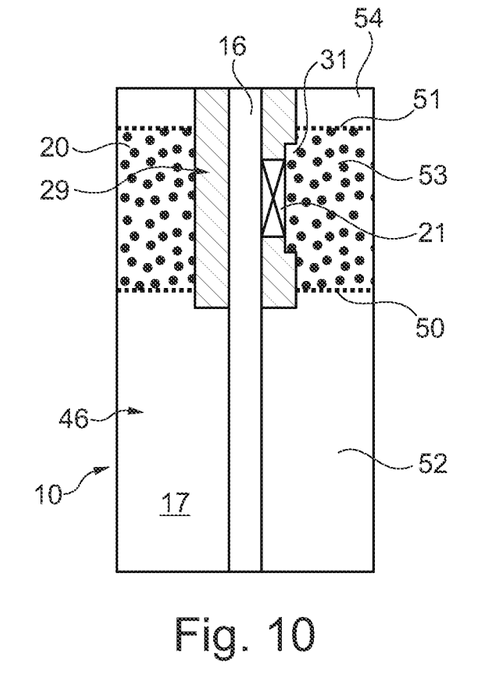
FIG. 10 shows an enlarged representation of a further embodiment of a vaporizer cartridge in partial section.
Figure 11:
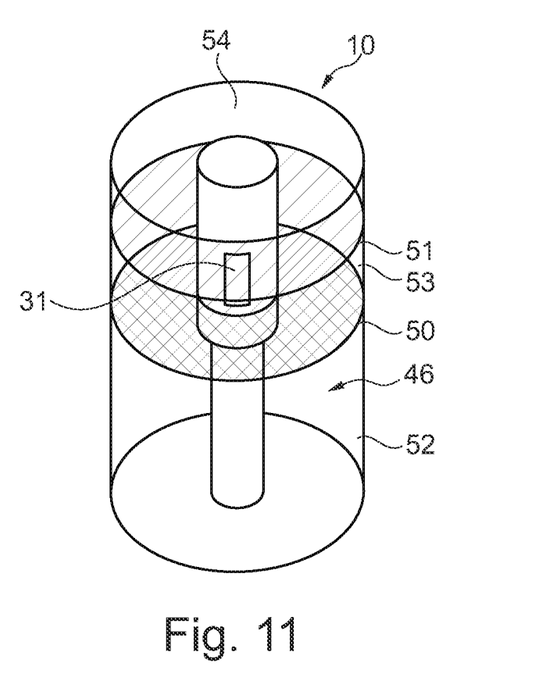
FIG. 11 shows the vaporizer cartridge according to FIG. 10.

In the variant of FIGS. 10 and 11, two structures 50 and 51, preferably grid structures, are provided which divide the inner space 46 into three regions 52, 53, 54. The two structures 50, 51 are arranged above and below the recess 31 with the heating member 21 in such a manner that the centre region 53 which serves to receive the wick member 20 (only indicated or not explicitly represented) covers the carrier element 29 at least in the region of the heating member 21. Liquid can be stored in other regions 52, 54. The securing means 25 of a mechanical type is formed by the housing wall 34 of the housing 33, the carrier element 29, the heating member 21 as well as the structures 50, 51 which jointly hold the granular wick member 20, here e.g. grains of sand, in position in front of the heating member 21. The structures 50, 51 ensure the fluid connection to the storage tank 17. Instead of grains of sand or other granular materials, e.g. an open-pored foam can also be arranged between the structures 50, 51.

Alternatively or cumulatively, the securing means 25 can be of a physical and/or chemical type such that the grains 24 are held in position by melting and/or hardening processes. The grains 24 can be fused e.g. with the hollow body 15 or the carrier element 29 or parts thereof. A type of cage in which loose grains 24 of the wick member 20 are held in position can be formed from grains 24 fused with one another of the wick member 20 in particular in combination with the heating member 21. Grains 24 can optionally also be fused with one another to form a lid 35. Instead of the grains 24, to form a receiving chamber 26 and/or a retaining element, expandable foam material can be used which is hardened in the position in which it surrounds or covers the vaporizer unit 19 in order to create a lid 35 with which the wick member 20 is held in position.

In further embodiments, not represented explicitly, the securing means 25 for the granular wick member 20 is alternatively or cumulatively of a magnetic type such that the grains 24 are formed to be at least partially magnetic and magnets which are arranged in the region of the wick member 20 hold the grains 24 in position. Optionally, the securing means 25 is alternatively or cumulatively of an electrostatic type such that the grains 24 are at least partially electrically charged and electric fields which are present in the region of the wick member 20 hold the grains in position.

The securing means 25 are configured and adapted entirely or partially optionally for permanent or temporary securing. Parts of the securing means 25 are preferably configured and adapted for permanent securing, for example, by constructive components in the form of the side walls 32, the heating member 21, the cover elements 28/lids 35 or the like which hold the wick member 20 in position in the mounted state up to the end of the service life of the vaporizer cartridge 10. Other parts of the securing means 25, which facilitate in particular the introduction of the wick member 20, are intrinsic to the wick member 20 itself, for example, shock-frozen liquid/granulate pastes which hold in position or hold together the wick member 20 up until final installation in the vaporizer cartridge 10.

Figure 1:
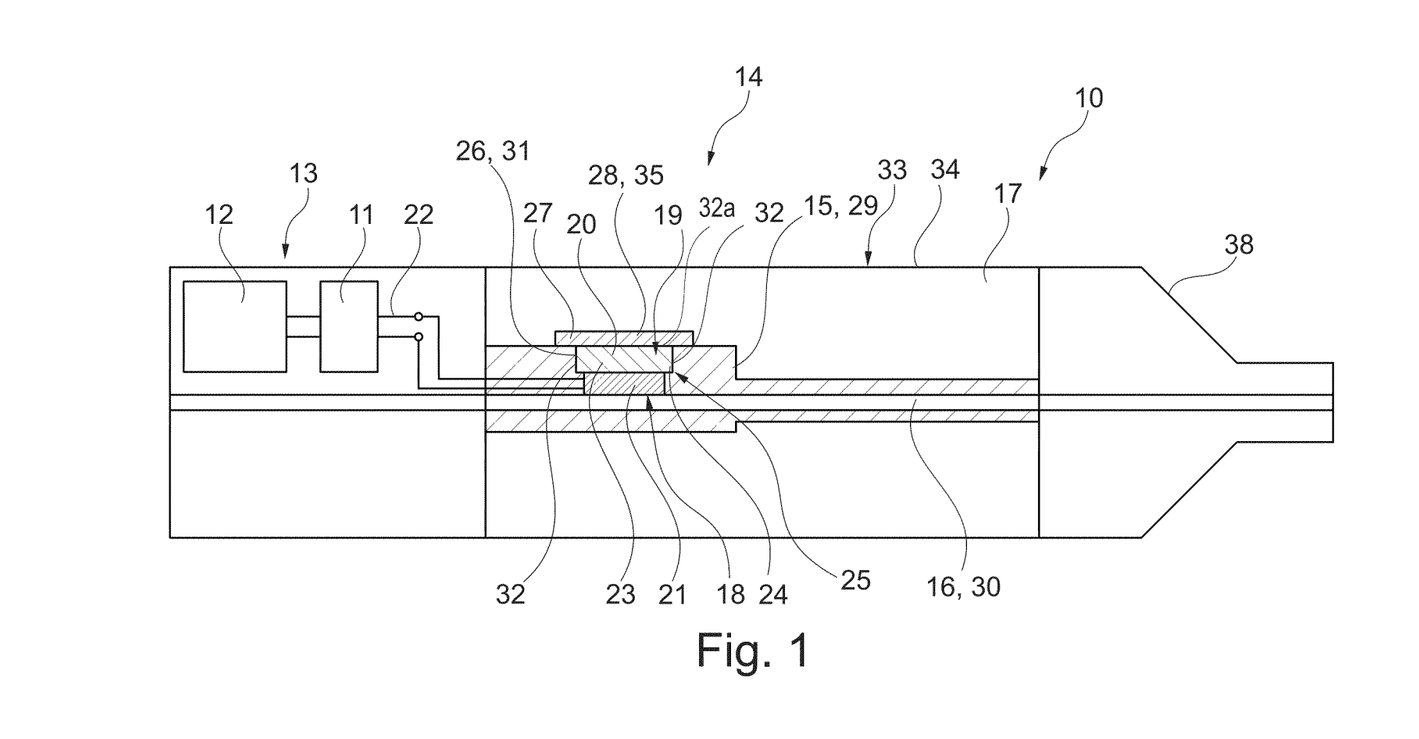
FIG. 1 shows a schematic representation of a preferred embodiment of an inhaler according to the invention with cartridge carrier and vaporizer cartridge in partial section.

The mode of operation of the inhaler 14 according to the invention is described by way of example on the basis of an E-cigarette as an inhaler 14 in particular in relation to FIG. 1. The inhaler 14 is configured and adapted for the inhalation of vapour enriched with active ingredients and comprises a cartridge carrier 13 at least comprising an electronic control unit 11 and an energy source 12 as well as a vaporizer cartridge 10 which is characterised according to the invention described herein.

A consuming person sucks e.g. on a mouthpiece 38 of the inhaler 14 which is formed from the cartridge carrier 13 and the vaporizer cartridge 10, wherein a liquid which contains, for example, glycerine, propylene glycol and possibly further active ingredients and/or flavourings is located in the storage tank 17 of the vaporizer cartridge 10. As a result of suction, a vacuum is generated in the flow channel 16, which vacuum itself activates the control unit 11 e.g. via a sensor, not represented. The control unit 11 controls the heating member 21 which is supplied with energy by the energy source 12. Liquid from the storage tank 17 is transported by means of the wick member 20 at least initially in a capillary manner through the microchannels 23 out of the storage tank 17 in the direction of the heating member 21. At or in the heated heating member 16, the liquid is converted into vapour, wherein the heating member 16 transports the liquid or the vapour formed therefrom as a result of the liquid- and vapour-permeable structure in the direction of the flow channel 16 and discharged to it. The vapour mixes in the flow channel 16 with the air flow and is sucked in and inhaled by the consuming person.

The invention claimed is:

1. A vaporizer cartridge as a component of an inhaler, comprising:
   a hollow body with a continuous flow channel;
   a storage tank for storing liquid, the storage tank having an access opening to the flow channel;
   a vaporizer unit arranged in a region of the access opening and extending over an entirety of the access opening, the vaporizer unit comprising a wick member and a heating member, wherein the vaporizer unit is formed to be liquid-permeable in such a manner that liquid is conveyed at least initially in a capillary manner from the storage tank through the vaporizer unit in a direction of the flow channel;
   wherein the wick member is formed from a plurality of granular grains which, as a result of their fill and/or formation, form microchannels which extend, for an establishment of a fluid connection between the storage tank and the flow channel, continuously from an entry side of the wick member to an exit side of the wick member;
   an additional securing means configured and adapted to hold the wick member in a position in the region of the access opening in a manner which maintains the fluid connection;
   wherein the securing means is of a physical and/or chemical type such that the plurality of granular grains are held in position by melting and/or precipitation-hardening processes;
   wherein the plurality of granular grains of the wick member are fused directly with the hollow body; and
   wherein at least a cover element is formed from the fused plurality of granular grains from at least one part of the wick member.

2. The vaporizer cartridge according to claim 1, wherein the securing means is of a mechanical type such that a receiving chamber is defined that is enclosed on all sides with an opening for introduction of the wick member, the receiving chamber being formed from components of the vaporizer cartridge or parts thereof and the opening is closed with the cover element, wherein the receiving chamber is formed to be liquid-permeable at least in sections.

3. The vaporizer cartridge according to claim 2, wherein:
   the vaporizer cartridge comprises a carrier element which forms the hollow body and, on the one hand, has a through-opening forming the flow channel and, on the other hand, has a recess for receiving the wick member; and
   the recess forms side walls of the receiving chamber and the recess is delimited towards the storage tank and towards the flow channel in each case by a liquid-permeable structure.

4. The vaporizer cartridge according to claim 3, wherein:
   the plurality of granular grains of the wick member are held in position by a sieve in such a manner that the sieve, together with the side walls delimiting the receiving chamber and a heating member formed separately from the wick member, encloses a volume of the wick member.

5. The vaporizer cartridge according to claim 2, wherein the cover element is a solid or soft lid.

6. The vaporizer cartridge according to claim 5, wherein the lid covers the entire hollow body including the opening of the receiving chamber, the lid being formed to be liquid-permeable at least in sections.

7. The vaporizer cartridge according to claim 5, wherein the lid is a sleeve which is displaceable in a longitudinally axial or rotational manner with respect to the hollow body and which is formed to be liquid-permeable at least in sections.

8. The vaporizer cartridge according to claim 5, wherein the lid has a wound fleece strip or is formed from a wound fleece strip.

9. The vaporizer cartridge according to claim 1, wherein the plurality of granular grains of the wick member form their own closed receiving chamber which is liquid-permeable at least in sections.

10. The vaporizer cartridge according to claim 1, wherein the securing means is of a magnetic type such that the plurality of granular grains are formed to be at least partially magnetic and magnets which are arranged in a region of the wick member hold the plurality of granular grains in position.

11. The vaporizer cartridge according to claim 1, wherein the securing means is of an electrostatic type such that the plurality of granular grains are at least partially electrically charged and electric fields which are present in a region of the wick member hold the plurality of granular grains in position.

12. The vaporizer cartridge according to claim 1, wherein the securing means is configured and adapted for a permanent or a temporary securing.

13. An inhaler, configured and adapted for the inhalation of vapour enriched with active ingredients, comprising:
   a cartridge carrier comprising at least one electronic control unit and an energy source; and
   as a vaporizer cartridge according to claim 1.

* * * * *